United States Patent [19]

Davis, Jr. et al.

[11] Patent Number: 4,482,634
[45] Date of Patent: Nov. 13, 1984

[54] CHEMICAL FLOOD TESTING METHOD

[75] Inventors: Lorne A. Davis, Jr.; Dale F. Brost; Helen K. Haskin, all of Houston, Tex.

[73] Assignee: Texaco Inc., White Plains, N.Y.

[21] Appl. No.: 336,136

[22] Filed: Dec. 31, 1981

[51] Int. Cl.³ .............................................. E21B 49/02
[52] U.S. Cl. ............................... 436/31; 324/585 A; 166/252; 73/153
[58] Field of Search ..................... 436/31, 2, 150, 25, 436/173; 166/252, 250, 66; 324/376, 316, 303, 58.5 A; 73/153

[56] References Cited

U.S. PATENT DOCUMENTS

| | | | |
|---|---|---|---|
| 4,022,276 | 5/1977 | Drehr et al. | 324/303 |
| 4,206,809 | 6/1980 | Jones | 166/252 |
| 4,233,559 | 11/1980 | Hoberg et al. | 324/58.5 A |
| 4,273,187 | 6/1981 | Satter et al. | 166/250 |

OTHER PUBLICATIONS

Parsons, Society of Petroleum Engineers Journal, 8/75, pp 302-309.

*Primary Examiner*—Hiram H. Bernstein
*Attorney, Agent, or Firm*—Jack H. Park; Ronald G. Gillespie

[57] ABSTRACT

A method of testing a chemical for use in an enhanced recovery of oil from an earth formation includes obtaining a test core of an earth formation. The test core is cleaned and then subjected to a predetermined sequence of events similar to that which the reservoir has experienced. The test core is flooded with a chemical to be tested and the chemical is then driven from the test core with a drive liquid. The test core is irradiated with a beam of electromagnetic energy at a microwave frequency. An indication representative of the effectiveness of the chemical in the test core is derived in accordance with the electromagnetic energy that has passed through the test core.

26 Claims, 10 Drawing Figures

CHEMICAL FLOOD TESTING METHOD

BACKGROUND OF THE INVENTION

1. Field of the Invention

The present invention relates to earth formation analysis in general and, more particularly, to microwave spectrometry of an earth formation core and to surfactant testing.

2. Prior Art

Heretofore, a method of analyzing in situ oil-brine saturation of samples of an earth formation in a laboratory were of the type described by R. W. Parsons, MICROWAVE ATTENUATION - A NEW TOOL FOR MONITORING SATURATIONS IN LABORATORY FLOODING EXPERIMENTS, Society of Petroleum Engineering Journal (August 1975, Volume 15, 302-309). However, these instruments are based upon a microwave frequency of about 21 GHz. Several difficulties arise from the high power level required at this frequency to penetrate the water-saturated rock slabs used in the experiments. Power levels are on the order of several hundred milliwatts, far above established safe exposure limits. Because of this, adequate precaution must be taken to insure a safe working environment. The use of high power levels cause several instrumental complications.

To generate several hundred milliwatts of microwave power at 21 GHz, klystron sources are used which require specialized power supplies for stable operation and also requires considerable maintenance. Further, since a wide range of power is transmitted through a core during a flooding experiment, precision attenuators are required to maintain the power level within the range limits of the detector. Isolators must be used to shield the klystron from reflective radiation. Tuners are employed to precisely match impedances from maximum power transfer efficiency. Microwave power is directed to and from the porous medium by detected by a thermocouple or crystal based power meter, converted to a voltage and passed to a logarithmic amplifier. The output is proportional to the water saturation of the core.

In addition to the undesirable expense and complexity of the aforementioned designs, practical application has been restricted to epoxy-coated flat slabs of Berea sandstone having typical dimensions of 2.54 cm thick, 10.2 cm wide and up to 122 cm long.

The present invention by utilizing a small cross-sectional area test core is capable of operating throughout the microwave frequency range at lower power level than Parsons and does not require the safety equipment nor the complex instrumentation required in the aforementioned Parsons apparatus. The present invention eliminates isolators and does not have to be tuned.

SUMMARY OF THE INVENTION

A method of testing a chemical for use in an enhanced oil recovery in an earth formation includes obtaining a test core of an earth formation. The test core is cleaned and then subjected to a predetermined frequency of events similar to that which the reservoir has experienced. The test core is filled with a chemical to be tested and the chemical is then driven from the test core with a drive liquid. The test core is irradiated with a beam of electromagnetic energy at a microwave frequency. An indication representative of the effectiveness of the chemical in the test core is derived in accordance with the electromagnetic energy that has passed through the test core.

One object of the present invention is to provide a rapid and simple method of surfactant testing to aid in surfactant selection prior to chemical flooding of a petroleum reservoir in enhanced oil recovery.

Another object of the present invention is to test an enhanced oil recovery operation by core flood testing.

The foregoing and other objects and advantages of the invention will appear more fully hereinafter from a consideration of the detailed description which follows, taken together with the accompanying drawing wherein two embodiments of the present invention are illustrated by way of example. It is to be expressly understood, however, that the drawings are for illustration purposes only and are not to be construed as defining the limits of the invention.

DESCRIPTION OF THE INVENTION

Figure 1:
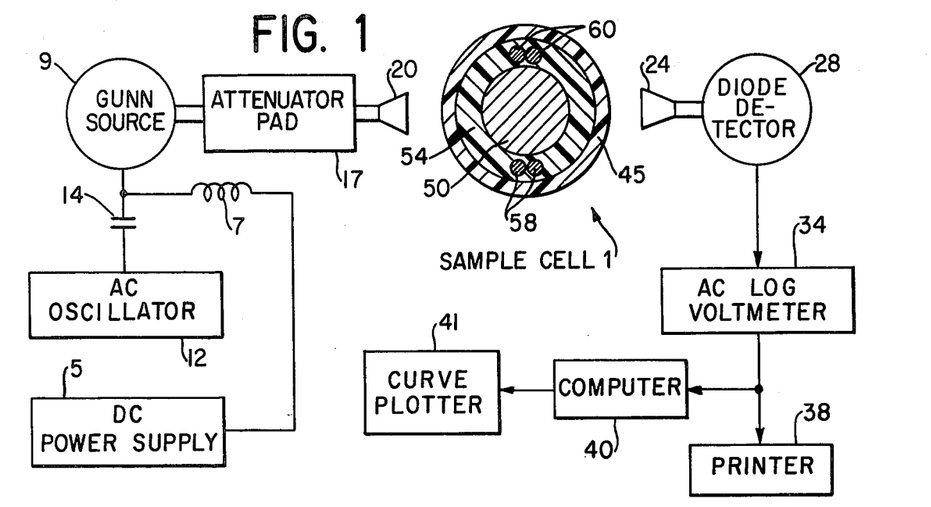
FIG. 1 is a simplified block diagram of a microwave core monitor constructed in accordance with the present invention.

Referring now to FIG. 1, a sample cell 1 constructed as hereinafter disclosed, is subject to microwave energy. Microwave energy is herein defined as being electromagnetic energy provided at a microwave frequency. In providing microwave energy, a direct current power supply 5 provides DC power through a coil 7 to a Gunn microwave source 9 of the type that is manufactured by Racon, Inc. as their part number 10014-102-02. An oscillator 12 provides an AC voltage as a predetermined frequency through a capacitor 14 to Gunn source 9. A preferred frequency of the AC voltage is 1 KHz. Gunn source 9 provides the microwave energy, at a preferred frequency of 10.525 GHz, whose amplitude oscillates at the 1 KHz frequency. Source 9 provides the microwave energy to an attenuator pad 17 which provides the microwave energy in turn to a horn antenna 20. It should be noted that a horn antenna is used because the Gunn source 9 is being operated in an X-band mode. It may be desired to operate Gunn source 9 at a preferred frequency of 24.125 GHz, which is in the K-band mode and makes monitoring more independent of temperature and salinity in regards to the sample in sample cell 1. The determination of whether to use X-band or K-band is also in part determined by the core size selected. A preferred power output for the X-band is 10 mw while for the K-band is anything greater than 50 mw to safe operating levels. Horn antenna 20 is replaced by a dielectric rod antenna and Gunn source 9 is of a type similar to that manufactured by Plessey Optoelectronics and Microwave Ltd., as their part GD0131 when operating in a K-band mode. Further, oscillator 12 may be omitted in K-band operations.

The microwave energy passing through sample cell 1 is received by another horn antenna 24 in X-band mode, or a dielectric rod antenna in the K-band mode, and provided to a diode detector 28. Diode detector 28 provides an electrical signal, corresponding to the detected microwave energy, to an AC log voltmeter 34. Voltmeter 34 provides a visual readout and also an output to a printer 38 and to a computer 40 which prints out the detected microwave energy. Computer 40 controls a curve plotter 41 in accordance with the output from voltmeter 34.

Figure 2:
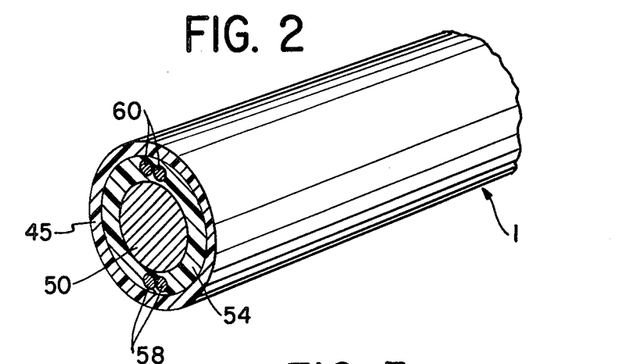
FIG. 2 is a graphical representation of the sample cell shown in FIG. 1.

Referring now to FIGS. 1 and 2, sample cell 1 includes a cylindrical test core 50 of an earth formation, having a preferred diameter in the range of from a $\frac{1}{2}$ inch to $\frac{3}{4}$ inch and a preferred length in the range from $2\frac{3}{4}$ inches to 3 inches, is maintained in a hard plastic tubular shell 45 by epoxy 54. Another way to define the length is to say that the length is substantially equal to the distance along the longitudinal axis of test core 50 that is intercepted by the microwave beam. Shell 45 may be made of a machineable hard plastic such as chlorinatedpolyvinylchloride or polyvinylidinediflouride. Embedded in epoxy 54 are absorber rods 58 and 60. In one particular application there are four such microwave absorber rods 58 and 60. One pair of absorber rods 58 are located along side of test core 50 while another pair of absorber rods 60 are located diametrically opposite along side of test core 50. It should be noted that test core 50 is oriented with relation to antenna 20 and 24 in a manner so that a straight line from antenna 20 to antenna 24 will be perpendicular to an axis passing through both pairs of absorber rods 58 and 60. Absorber rods 58 and 60 prevents the microwave energy from circumventing the core 50 and being detected by diode detector 28 so as not to cause erroneous readings and so that the microwave energy detected by detector 28 is the microwave energy that has passed through test core 50 and 60. Microwave absorber rods 58 are made of ferrite loaded epoxy. Preferred attenuation coefficient for such material is 46 dB/cm at 10 GHz.

The apparatus as hereinbefore described may be used to screen surfactants prior to core flood testing and has the following advantage: (1) the actual formation material is used to test the surfactants, (2) the screening is rapid and (3) highly economical.

Figure 3:
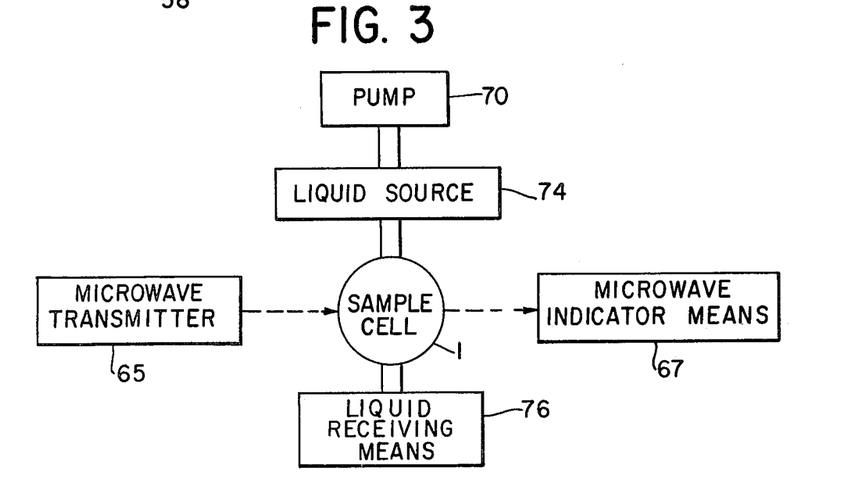
FIG. 3 is a simplified block diagram of a surfactant monitor, constructed in accordance with another embodiment of the present invention.

In this regard, and with reference to FIG. 3, microwave transmitter 65 includes DC power supply 5, coil 7, Gunn source 9, AC oscillator 12, capacitor 14, attenuator pad 17 and antenna 20, all of which function as previously described. A microwave indicator means 67 includes antenna 24, diode detector 28, AC log voltmeter 34 and printer 38; all of which function as previously described. A pump 70 pumps distilled water to a liquid source 74. Liquid source 74 includes a conventional type free floating piston (not pumped in distilled water causes the piston to expell the liquid from liquid source 74. Further liquid source 74 is capable of readily having one liquid replaced by another liquid for reasons hereinafter explained.

The expelled liquid from liquid source 74 enters sample cell 1, which is adapted as hereinafter explained for the surfactant tester of FIG. 3, until sample cell 1 is completely filled. Excess liquid will pass through sample cell 1 into liquid receiving means 76 which may be test tubes or any other suitable container.

Figure 4:
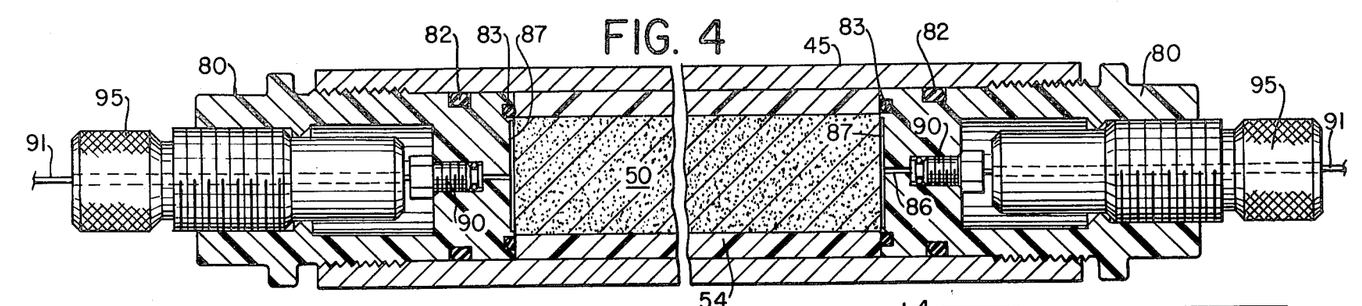
FIG. 4 is a detailed drawing of the sample cell shown in FIG. 1.

Referring now to FIG. 4, shell 45 is machined to have female threads at both ends and test core 50 is centered in shell 45 and held in place by epoxy 54 containing absorber rods 58 as hereinbefore described. End plugs 80 are screwed into shell 45 at each end with O-rings 82 and 83 in place. O-rings 82 provides sealing between shell 45 and end plugs 80 so that no liquid can escape from sample cell 1 while O-rings 83 provides sealing between epoxy 54 and end plugs 80 so that the liquid flows through test core 50.

Each end plug 80 has a channel 86 from an internal face 87 to a bottom tap where a conventional type chromatograph fitting 90 is seated having tubing 91 connected to it. Tubing 91 passes through a support bolt 95 which is made of machineable plastic and adapted to be threaded into end plug 80. Support bolt 95 holds chromatograph fitting 90 in place inside end plug 80 and supports tubing 91 as it passes through support bolt 95. The entire end plug-support bolt assembly has a very low dead volume as compared to a conventional manner of providing end plugs for sample cell 1. Dead volume is any volume in the test arrangement that is not the pore volume of test core 50. Large dead volume can render pore volume determination and usage erroneous.

SURFACTANT SCREENING

Production of crude oil from a reservoir in an earth formation generally will experience several phases. In an initial phase the natural reservoir pressures, the porosity of the reservoir's earth formation and the fluidity of the crude oil permits production without assistance other than pumping. However, there comes a time when there is still considerable crude oil in the reservoir, but the pressure is such that assistance is necessary. The assistance is provided with a water flood in a secondary recovery operation using a drive liquid, such as salt water, to drive the crude oil to a producing well.

Even after secondary recovery operations, there still remains considerable in-place crude oil. At this time most reservoirs are subjected to enhanced oil recovery operation using a chemical flood. A chemical flood utilizes a surfactant which is driven through the reservoir by a liquid, usually salt water, with a polymer slug between the drive liquid and the surfactant. The surfactant decreases the interfacial tension between the crude oil and the in-place brine in the reservoir's earth formation so that the crude oil so released is driven to the producing well. Again not all of the in-place crude oil is so affected so that even after a chemical flood there is residual crude oil in the reservoir.

There are many different types of surfactants that will react with the crude oil, the salt water and the reservoir's earth formation in different ways. Many tests are conducted to select the best surfactant for a particular reservoir. However, the tests are lengthy. The present invention, as hereinafter described, provides an initial screening process so that only those surfactants showing promise for use in the reservoir need be subjected to the longer time consuming tests.

With reference to FIG. 3, sample cell 1 is already in existence or, preferable made in which test core 50 is obtained from the reservoir's earth formation where a selected surfactant is intended to be used. Initially, microwave transmitter 65 irradiates sample call 1 while sample cell 1 has no liquid in it so that a first reading is obtained from microwave indicating means 67 of test core 50 of sample cell 1 as if it were filled only with oil. Initially, the liquid in liquid source 74 is salt water, preferaly of substantially the same salinity and hardness as the water used to flood the reservoir where a selected surfactant will be used, the salt water is pumped into sample cell 1 at an arbitrarily selected velocity of 20 feet per day. Microwave transmitter 65 is still irradiating sample cell 1 with microwave energy. When salt water appears entering liquid receiving means 76, a second reading provided by microwave indicating means 67 is representative of the salt water in sample cell 1.

The liquid in liquid source 74 is changed from salt water to crude oil from the reservoir and pump 70 is operated until only crude oil enters liquid receiving means 76. A third reading provided by microwave indicating means 67 at this time is representative of residual salt water to oil injection. A conventional material balance is carried out at this time to provide an oil saturation measurement.

The crude oil in liquid source 74 is replaced with salt water and the operation is repeated, i.e., until only salt water enters liquid receiving means 76, a fourth reading at this time corresponds to residual oil to water flood. Again, a material balance yields a measurement of the new oil saturation.

Figure 5:
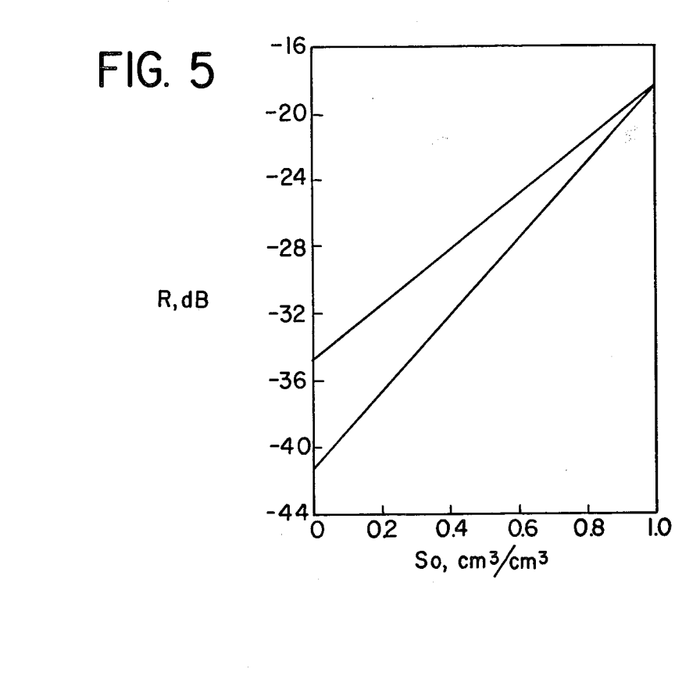
FIGS. 5 and 6 are graphs of typical calibration curves for the operation of the present invention in X-band and K-band microwave modes, respectively.
Figure 6:
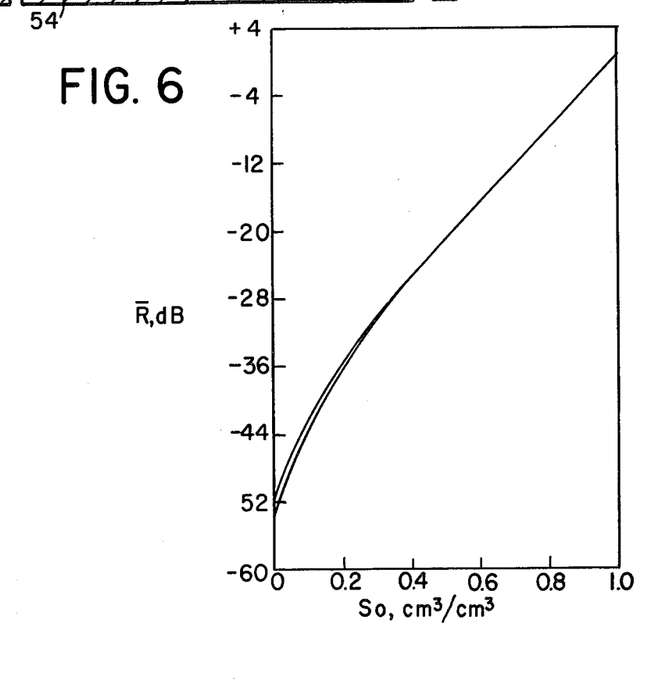

The four readings along with the material balance measurements constitute calibration data. Computer 40 controls curve plotter 41 to generate a curve in accordance with the calibration data. FIGS. 5 and 6 show typical calibration curves for X-band and K-band operation respectivel The next step of surfactant screening is to pump a surfactant into sample cell 1 from liquid source 74 at the test core 50 so as to standardize the screening of the surfactants. No reading is necessary at this time. A postsurfactant flush is then initiated using salt water having substantially the same salinity as the expected surfactant drive water in the field. A reading is taken when no further oil enters liquid receiving means 76 which is then utilized with the generated calibration graph to determine the residual oil saturation after chemical flood.

By using the foregoing method, several different sample cells 1 may be constructed from the reservoir earthen material since test core 50 is small in size. This facilitates screening of different surfactants.

In another embodiment, only one particular sample cell 1 is used to test the different surfactants. In this method the calibration readings, and hence computer 40 and curve plotter 41, may be eliminated and the readings of residual oil saturation after chemical flood may be used directly in the selection of a surfactant. This method requires the following summarized steps for each surfactant test.

1. Saturate test core 50 with salt water.
2. Flood test core 50 with crude oil to residual water.
3. Flood test core 50 with salt water to residual oil to water flood.
4. Flood test core 50 with surfactant.
5. Flush surfactant from test core 50 with salt water.
6. Obtain a reading from microwave indicating means 67 which is representative of the residual oil saturation after chemical flood.
7. Wash test core 50 of sample cell 1.

The washing step is accomplished by washing with fresh water at maximum rate that pressure will allow. After clean water leaves sample cell 1, 2-propanol is flushed through sample cell 1 to remove any absorbed surfactant. A preferred mixture of 80% toluene and 20% methanol by volume is flushed through test core 50 to sample cell 1 to wash out residual crude oil followed by another wash of 2-propanol. Finally test core 50 in sample cell 1 is washed with fresh water and sample cell 1 is then ready to be used for surfactant screening again.

CORE FLOOD TESTING

Since it is desirable that a portion of the reservoir formation be subjected to a flooding test, the Parsons' instrumentation could not be used since it requires a slab of the formation. Such a slab either cannot be obtained from a reservoir's formation or it is not readily obtainable. The conventional alternative to Parsons is to use a field core from the reservoir formation and test it using a material balance technique. However, because of the small quantities of liquid used in the conventional core flood testing the associated error in determining the tertiary oil recovery efficiency may be well in the neighborhood of 16%.

The present invention provides the same information as the conventional core flood test such as the initial oil saturation before water flood averaged over the core length, the residual oil saturation after the water flood averaged over the core length, the residual oil saturation of the chemical flood averaged over the core length, and water flood and chemical flood recovery efficiency, which is the ratio of the amount of oil removed to the amount of oil in place with greater accuracy in the neighborhood of 1%. The present invention further provides an indication of oil saturation distribution along the length of the test core.

Further, the conventional core flood method utilizes a core one to six feet long which covers the stratum but is not representative of the formation at a particular level within the stratum so that there is an average determination. The present invention, since it uses small cores as hereinafter explained, can reduce the level within the stratum to a matter of inches as opposed to the several feet used in the conventional method. Further, several cores can be made utilizing the present invention as opposed to a conventional type of core resulting in greater economy.

Figures 7, 8:
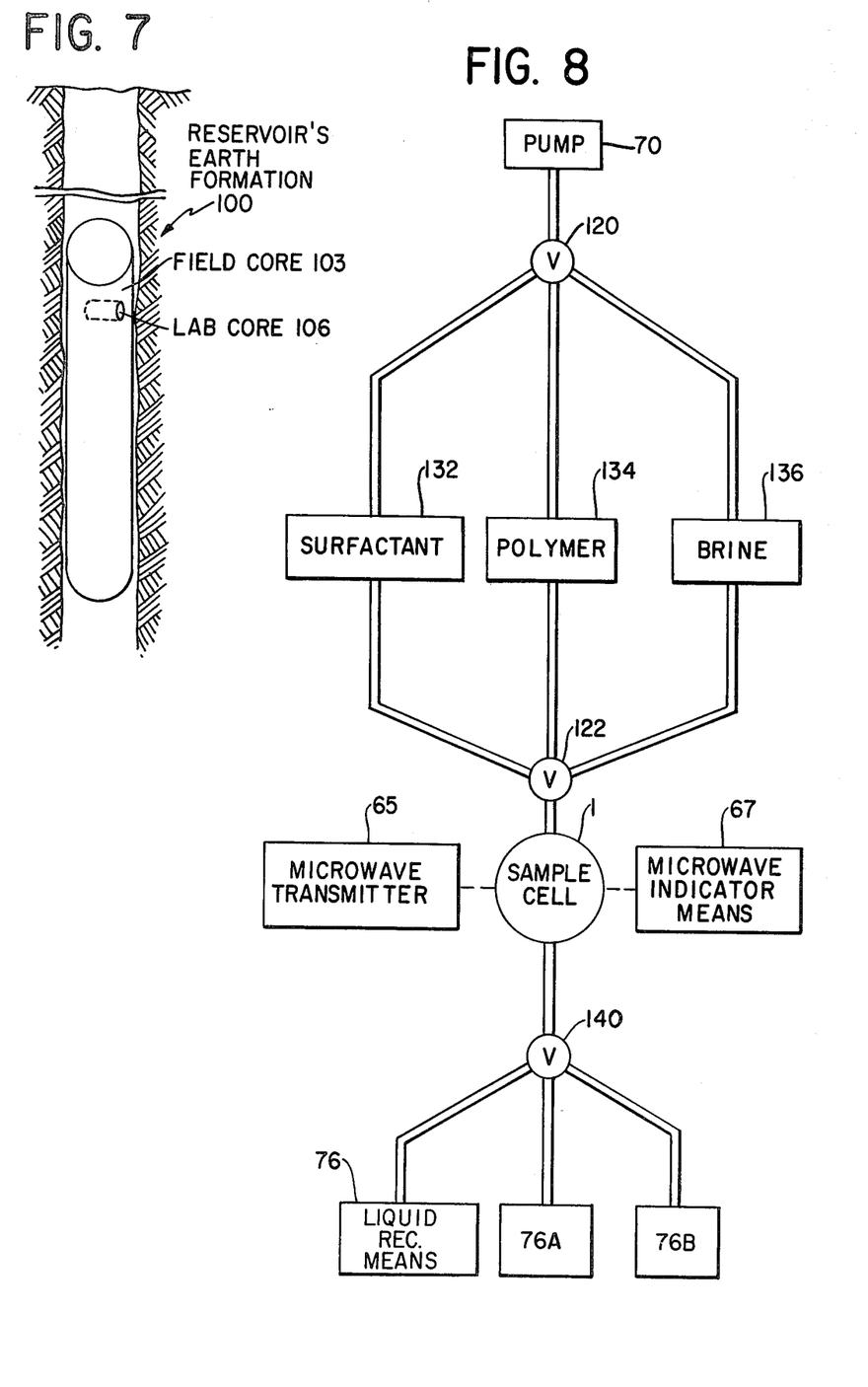
FIG. 7 illustrative shows the relationship of a field core, a lab core and a reservoir's earth formation.
FIG. 8 is a simplified block diagram of a core flood tester constructed in accordance with the present invention.

Referring to the FIG. 7, a reservoir's earth formation 100 has a field core 103 removed from it by conventional coring methods. FIG. 7 also shows the relationship of field core 103 to the reservoir's earth formation 100. Field core 103 is then cored in a laboratory or any suitable location to extract lab core 106. As noted previously in describing test core 50, which essentially is made up of lab cores 106 for cylindrical test core 50, has a preferred diameter in the range of from a one-half inch to three-quarter inch. If test core 50 has rectangular cross section, lab core 106 will also have rectangular cross section having one side a preferred size of three-quarter inch and another side of five-eighth inch. It should be noted that the main difference between test core 50 and lab core 106 is that the length of lab core 106 will vary depending on where it is extracted from field core 103. Of course, if the field core 103 has a rectangular cross section, then the length of lab cores 103 will be constant. The variation in length of lab core 103 is of no importance to the present invention.

Generally, the stratum of reservoir's earth formation 100 will vary in thickness with a typical minimum thickness of two feet increasing up to in some areas as much as eighteen feet. The geology and mineralogy may be relatively constant or change every few inches down the field core. In conventional-type laboratory flood testing, the field core is generally 4 inches in diameter and 4 feet to 16 feet long, however, since the permeability of reservoir earth formation 100 generally is in a horizontal direction and not in a vertical direction, the field core itself is not used directly but is cut into 2 inch diameter, three inch long segments which are butted together to form the conventional test core. The problem with this arrangement is that the characteristics determined can only be average characteristics of the stratum over the length of the original field core. By utilizing lab cores in the manner hereinafter explained the characteristics of the earth formation can be narrowed down to an inch-and-a-half to possibly two-inch level of the stratum segment. Further, by repeated use of lab cores throughout the length of the field core a distribution of the characteristics throughout the length of the field core, and hence that portion of the stratum, can be determined as opposed to the conventional average characteristics.

Typically, with the preferred dimensions hereinbefore mentioned, a total of six lab cores 106 can be obtained from one level of field core 103. Lab cores 103 are then butted together to form a long test core 114 (not shown) for core flooding testing.

Long test core 114 is not shown for ease of understanding. Basically, with reference to FIG. 4, the major difference between FIG. 4 for sample cell 1 in surfactant screening as opposed to core flood testing is the length of the test core. In this regard, test core 50 shown in FIG. 4 will be replaced by long test core 114. The length of long test core 114 may vary from two to six feet as desired. Sample cell 1 has markings designating predetermined distances of sample cell 1 for reasons hereinafter explained.

Referring now to FIG. 8, in core flood testing pump 70 pumps a liquid through valve means 120. Valve means 120 in conjunction with valve means 122 in effect controls which liquid is going to be provided to sample cell 1. In one mode, the output from valve means 120 is provided to a surfactant reservoir 132, in another mode, the output from valve means 120 is provided to a polymer reservoir 134, and a third mode results in the output being provided to a brine reservoir 136. The output of the surfactant reservoir 132, polymer reservoir 134 and the brine reservoir 136 are provided to three different inputs of valve means 122, thus for one mode pump 70 in effect pumps surfactant from surfactant reservoir 132 into sample cell 1; in a second mode, pump 70 in effect pumps polymer from polymer reservoir 134 into sample cell 1, and in the third mode brine is pumped into sample cell 1.

The liquid from valve means 122 passes through sample cell 1 to another valve means 140, which is operated in conjunction with valve means 120 and 122 to pass liquid from sample cell 1 to liquid receiving means 76, 76A or 76B. It should be noted that elements having the same numerical identification with a different suffix operated and are connected in a similar manner as the element with the same numerical designation without a suffix.

Figure 9A:
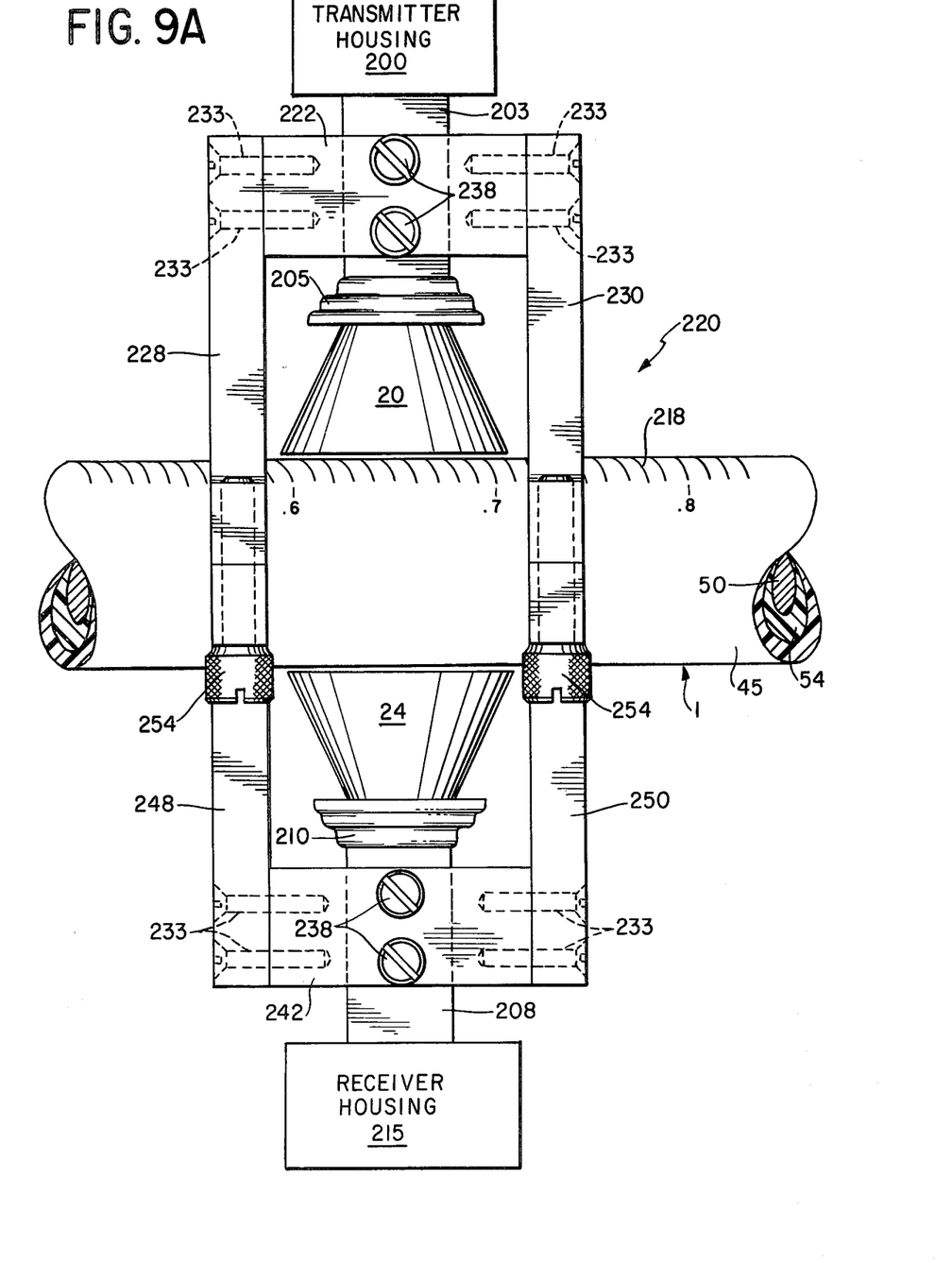
FIGS. 9A and 9B are assembly type drawings of a fixture used in the core flood tester.
Figure 9B:
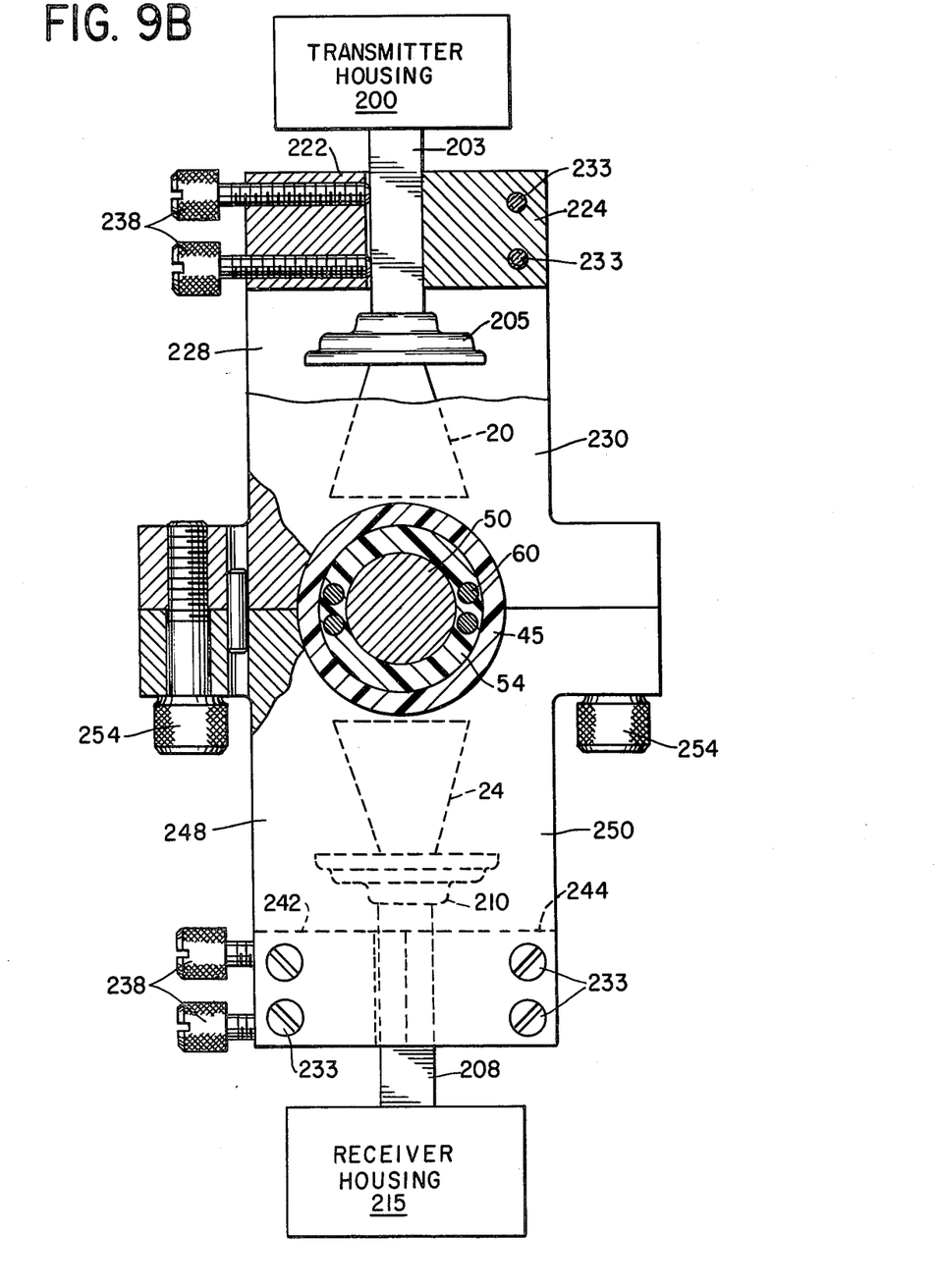

With reference to FIGS. 9A and 9B transmitter housing 200 houses coil 7, gunn source 9, AC oscillator 12, capacitor 14 and alternator pad 17. DC power supply 5 is not contained within the housing 200 but is electrically connected to it. DC power supply 5 is not shown in FIG. 9A. A wave guide 203 is connected to horn antenna 20 by way of an adaptor 205. Receiver horn antenna 24 is connected to a wave guide 208 by an adaptor 210 which in turn is connected to receiver housing 215. Receiver housing 215 houses diode detector 28 and is electrically connected to AC log voltmeter 24 which in turn is connected to printer 38 and to computer 40. Computer 40 is connected to curve plotter 41, all of which are not shown in FIG. 9A and 9B for ease of understanding. Sample cell 1 has graduated markings 218 thereon. Horn antennas 20 and 24 are maintained in a predetermined relationship to each other by fixture 220. Fixture 220 may be made of any suitable material. By way of example fixture 220 has been made of a hard plastic material which includes a top front header 222 that is held in place along with a rear top header 224 by top side pieces 228 and 230. It should be noted that top front header 222 is designed to be removable and as such is held in place with screws 233 while on the rear top header is permanently affixed between top side pieces 228 and 230. As shown in FIG. 9B there is sufficient clearance between top header pieces 222 and 224 that allows wave guide 203 to pass between them so that horn antenna 20 may be properly positioned in relation to sample cell 1. Thumb screws 238 pass through top front header 222 and presses wave guide 203 against back top piece 224.

Similarly, a bottom portion of fixture 220 includes a removable front bottom piece 242, a non-removable back bottom piece 244 and bottom side pieces 248 and 250. Removable front bottom piece 242 is held in place with screws 233 and there is a passage between bottom pieces 242 and 244 for wave guide 208 which is held in a manner such that horn antenna 24 has the right relationship to sample cell 1 by thumb screws 238. The top portion of fixture 220 is separated from the bottom portion so that fixture 220 may be moved along sample cell 1 to align with various markings 218 on sample cell 1 for determination of a characteristic of a liquid contained in long test core 114 at a particular marking. The two halves of fixture 220 are clamped using thumb screws 254 which pass through clearance holes in bottom side pieces 248, 250 and are threaded into top side pieces 228 and 230, respectively, to provide a clamping action on sample cell 1.

The hard plastic material of fixture 220 may be lined with microwave absorber padding to eliminate any spurious responses due to reflection of the microwave energy by the material.

Of course, it would be obvious to one skilled in the art that the movement of fixture 220 which is done manually by an operator, may be facilitated by an automatic arrangement whereby a fixture that is specifically designed for the automatic arrangement and holding antennas 20 and 24 in proper alignment is moved a predetermined distance prior to each measurement.

The prior description contemplates operation at microwave frequencies in the X-band. As noted previously, gunn source 9 may be operated in the K-band during which all of the comments previously mentioned for K-band operation are equally applicable.

With reference to FIG. 8 valve means 120 and 122 are operated in conjunction with pump 70 to provide a small slug size of surfactant from surfactant source 132 to sample cell 1. A preferred size of the slug is approximately $\frac{1}{3}$ of the pore volume of long core 114 in sample cell 1. Valves 120 and 122 are then operated to provide the surfactant slug with polymer interface slug from polymer source 134 to sample cell 1 and through it. Again valve means 120 and 122 are then operated to drive the polymer and surfacant slugs with brine from brine source 136. All of the driving is done at a standard frontal velocity which by way of example maybe is roughly the flooding velocity of the reservoir. In this case, the selected velocity is 4 feet per day. That velocity may be restated as being 0.033 inch/minute. Since the liquids are moving at a slow frontal advance speed through test core 114, a fixture 198 is utilized to periodically scan sample cell 1 and readings are taken at predetermined intervals of sample cell 1.

Another application of the present invention is to use a slug size of 1/10 the pore volume of test core 114 in a core flood test and then determine the recovery efficiency at every tenth of the length of test core 114. A graph of the recovery efficiency versus slug size may be then developed. For example at 1/10 of the length of test core 114, the equivalent slug size is 1 pore volume and at 7/10 of the length, the equivalent slug size is 1/7 of the pore volume. The plotting of the slug size characteristics of different surfactants and/or polymer mobility control agent may then be used in selecting a suitable surfactant and/or polymer system.

The device of the present invention is a small core microwave monitor which may be used in the field or in the laboratory and which also may be used for surfactant screening or core flood testing.

An alternative method of calibration of multiple test core 50 prior to surfactant screening for K-band operation is
1. Saturate test core 50 with fresh water.
2. Flood with a predetermined mixture of 2-propanol and fresh water.
3. Obtain a reading from microwave indicating means 67 which is representative of oil saturation.

Steps 2 and 3 are repeated for different mixtures of 2-propanol and fresh water. As can be seen from the foregoing there are no material balance measurements required for calibration. At this point, the multiple core testing may be carried on as hereinbefore described.

The present invention may even be used at simulated field conditions of temperature to screen surfactants. The present invention as hereinbefore described can stand up to 300 psi of pressure. The present invention may also be used in an oven and the temperature raised to simulate reservoir temperature for the screening of surfactants. However, it should be noted that if the test temperature is close to or greater than the temperature ratings of the components of the microwave system, then an oven may be constructed in which only sample cell 1 is located in the oven and the microwave energy is directed through the walls of the oven and through sample cell 1.

What is claimed is:

1. A method of testing a surfactant for use in an enhanced oil recovery operation of a crude oil reservoir in an earth formation comprising the steps of:
    obtaining at least one core of an earth formation,
    cleaning said core,
    subjecting said core to a predetermined sequence of events similar to that which the reservoir has experienced,
    floodng the core with surfactant,
    driving the surfactant from the core with at least one drive liquid,
    irradiating the core with a beam of microwave energy so that a portion of the beam of microwave energy passes through the core,
    detecting the portion of the beam of microwave energy that has passed through the core, and
    deriving an indication of the effectiveness of the surfactant in accordance with the detection of the portion of the beam of microwave energy.

2. A method as described in claim 3 in which the subjecting step includes the steps of filling the core with crude oil, and
    flooding the core with water to drive out the crude oil.

3. A method as described in claim 4 in which the crude oil is the same crude oil from the reservoir, the flood water has the same salinity and hardness as the water used to flood the crude oil reservoir, and the drive liquid is the same type of drive liquid that will be used to drive the surfactant in the enhanced oil recovery operation.

4. A method as described in claim 1 further comprising preventing any portion of the beam of microwave energy from being detected that has not passed through said core.

5. A method as described in claim 2 in which the preventing step is accomplished by aligning microwave absorber rods with the core in a manner so that any portion of the beam of microwave energy not passing through said core is absorbed by said microwave absorber rods.

6. A method as described in claim 5 further comprising repeating all of the steps of the method of claim 5, with the exception of the step of obtaining a core, on said core for a different surfactant until all of the surfactants have been tested, and
    comparing the indication of the effectiveness of each surfactant to determine suitable surfactants.

7. A method of selecting a surfactant for use in the enhanced recovery of oil from the reservoir in an earth formation comprising the steps of
    obtaining two or more cores of an earth formation,
    passing a portion of a beam of microwave energy through a core,
    affecting the core with simulated reservoir conditions,
    deriving calibration data for each simulated condition in accordance with the portion of the microwave beam that has passed through the core,
    filling the core with a surfactant,
    driving the surfactant from the core with a liquid,
    deriving a characteristic of the effectiveness of the surfactant in accordance with the portion of the microwave beam that has passed through the core, and
    repeating all of the foregoing steps with the exception of the first-mentioned step for each remaining core using a difference surfactant for each core.

8. A metnod as described in claim 7 in which the affecting step includes deriving a first calibration point in accordance with the beam of microwave energy from the core when there is no liquid present in the core,
    filling the core with water so that a second calibration point derived in accordance with the received microwave energy corresponding to a water saturated core,
    driving the water in the core with crude oil so that a third derived calibration point is representative of residual water, and driving the crude oil in the core with water, so that a fourth calibration point derived from the received microwave energy is representative of residual crude oil after a water flood.

9. A method as described in claim 8 in which the characteristic derived is a quantitative evaluation of the residual oil remaining in the core after the use of the surfactant.

10. A method as described in claim 9 in which the cores are obtained from the reservoir's earth formation.

11. A method as described in claim 10 in which the water used to establish the second calibration point has the same salinity as the water used in the water flood of the reservoir.

12. A method as described in claim 11 in which the drive liquid has the same characteristics as the drive liquid that is expected to be used on the reservoir.

13. A method of testing fluid mechanics in a crude oil reservoir in an earth formation on which an enhanced oil recovery operation will be employed comprising the steps of
obtaining at least one core of earth formation,
cleaning said core,
first subjecting said core to a predetermined sequence of events similar to that which the reservoir has experienced,
second, subjecting said core to a predetermined sequence of events similar to the anticipated enhanced oil recovery operation,
irradiating the core with a beam of microwave energy,
detecting that portion of the beam of microwave energy that has passed through the core,
repeating the irradiating and the detecting steps at predetermined intervals along the length of the core during both subjecting steps, and,
deriving an indication of the effectiveness of the anticipated enhanced oil recovery operation.

14. A method as described in claim 13 in which the core is obtained from the crude oil reservoir's earth formation.

15. A method as described in claim 14 in which the first subjecting step includes the steps of filling the core with crude oil obtained from the crude oil reservoir, and,
recovering crude oil from the core using a water drive.

16. A method as described in claim 15 in which the second subjecting step includes
flooding the core with a chemical flood at the same rate as the chemical flood of the anticipated enhanced oil recovery operation; and,
the deriving step includes deriving an indication of a residual oil saturation of the core after the chemical flood.

17. A method as described in claim 16 in which the deriving step also includes
deriving an indication of oil saturation after the filling of the core with the crude oil but prior to the recovery step,
deriving an indication of a residual oil saturation of the core after the recovery step but prior to the chemical flooding step, and
deriving an indication of the recovery efficiency of the anticipated enhanced oil recovery operation.

18. A method as described in claim 17 in which the chemical flooding step includes
injecting a surfactant flood into the core,
injecting a polymer behind the surfactant slug, and,
driving the polymer and surfactant slug through the core with a brine.

19. A method as described in claim 18 in which the core includes lab cores butted end to end to form a preferred length of core.

20. A method as described in claim 19 in which the length of the core lies within a preferred range of 2 to 6 feet.

21. A method as described in claim 1 in which the microwave enery has a frequency which lies within the X-band frequency range.

22. A method as described in claim 21 in which the beam of microwave energy is provided at a preferred power level of substantially 10 milliwatts.

23. A method as described in claim 22 in which the microwave energy has a preferred frequency of 10.525 GHz.

24. A method as described in claim 1 in which the microwave energy has a frequency which lies within the K-band frequency range.

25. A method as described in claim 24 in which the beam of microwave energy is provided at a power level greater than at least 50 milliwatts but less than the safety standard power limit.

26. A method as described in claim 25 in which the microwave energy has a preferred frequency of 24.125 GHz.

* * * * *